Figure 3:
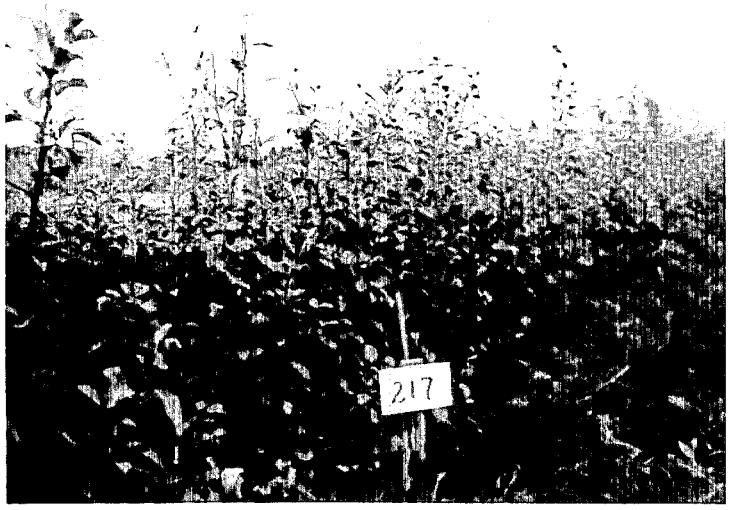

United States Patent [19]

Brooks

[11] Patent Number: Plant 5,468

[45] Date of Patent: May 14, 1985

[54] PEAR TREE

[75] Inventor: Lyle A. Brooks, Forest Grove, Oreg.

[73] Assignee: Carlton Nursery Company, Inc., Dayton, Oreg.

[21] Appl. No.: 534,180

[22] Filed: Sep. 20, 1983

[51] Int. Cl.[3] ..... A01H 5/03

[52] U.S. Cl. ..... Plt./36

[58] Field of Search ..... Plt./36

*Primary Examiner*—Robert E. Bagwill

*Attorney, Agent, or Firm*—Harvey B. Jacobson

[57] ABSTRACT

This invention relates to a new and distinct variety of pear tree (Variety 217) which is useful as a size-controlling pear rootstock. The new variety originated as a single seedling selected from a large group of pear seedling which were grown from open-pollinated seed. This seed was harvested from Old Home pear trees (*Pyrus communis*) growing in an isolated planting with Farmingdale pollinizers. Pear varieties grown on the understock of this new rootstock clone are approximately 85% of the size of like pear trees grown on Domestic Bartlett seedling rootstocks (*Pyrus communis*). This "semi-standard" selection can be easily increased by vegetative propagation methods using both hard and softwood cuttings. It is graft-compatible with all major pear varieties. It was selected for its non-rootsuckering habit, its high yield efficiency, its resistance to the Fireblight disease and its high tolerance of the Pear Decline disease. It is hardy, early bearing and has demonstrated good root-anchorage in all orchard sites where tested.

4 Drawing Figures

SUMMARY OF INVENTION

The original plant of this new variety was a member of a family of over 2000 pear seedlings which germinated from seed obtained from the Canadian Department of Agriculture Research Unit located near Summerland, British Columbia, Canada.

This seed, collected from open-pollinated Old Home pear trees (*Pyrus communis*) which were growing in an isolated experimental planting with Farmingdale pollinizers, was planted by the inventor in his nursery at Forest Grove, Oreg. in 1952.

Experimental objectives were to develop and/or determine by trial and selection, a series of clonal pear rootstocks which would fulfill several urgent needs of both the pear grower and the nurseryman. The most immediate needs were for rootstocks that are resistant to Fireblight (*Erwinia amylovora*) a common, debilitating bacterial disease of pear trees. Of equal importance and need were for rootstocks that are tolerant of the more recently described and very destructive disease of pear known as Pear Decline, which is a virus-like, mycoplasma-caused disorder affecting (plugging) pear phloem sieve tubes below the graft union. The plugged sieve tubes cause decline and death of trees grated on non-tolerant rootstocks.

Another experimental objective was to select from this seedling population rootstock clones which would root readily by cuttings and/or by other vegetative means. The most major additional objective was to determine and select a series of growth-controlling rootstock clones which would permit pear growers to develop plantings using tree spacing techniques tailored to known uniform tree sizes. Old Home × Farmingdale #217 has shown its usefulness by exhibiting the following characteristics which fulfill all of the original desired objectives. It has been chosen as the best of several "semi-standard" selections after nearly 30 years of orchard and nursery testing and evaluation.

Final selection was made in 1982 following tests which consisted of trial plantings and nursery evaluations which were carried out at Yakima, Wash.; Geneva, N.Y.; and Hood River, Salem, Medford, Corvallis, Dayton and Forest Grove, Oreg.

TEST AND EVALUATION RESULTS

1. Pear varieties grown on the rootstock of this variety are approximately 85% of the size of like pear trees grown on the most commonly used commercial pear rootstocks used in the trade. These are seedling rootstocks of Domestic Bartlett seed also known as Domestic pear seedlings (*Pyrus communis*). Trees grown on Bartlett seedling rootstocks are considered "standard" in size when established in the orchard and are used as the basis for all of our comparisons and measurements herein.

2. Because of its Old Home parentage, this new clonal rootstock exhibits high resistance to Fireblight infections whereas Domestic Bartlett seedling stocks are shown to be highly susceptible to this disease.

3. Trees propagated on this clonal stock proved to be Pear Decline tolerant in all tests and trial orchard plantings. In comparison, decline symptoms were common on trees grafted to Domestic Bartlett seedling rootstocks as well as on trees grated to several other seedling rootstock types being evaluated.

4. The new pear rootstock clone has been virus-indexed and found to be free of all known virus diseases of pear.

5. Less than one half of 1% of the trees tested on this stock showed a tendency to throw rootsuckers.

6. Old Home × Farmingdale #217 stocks gave the highest yield efficiency ratings of all rootstocks tested. Yield efficiency was determined by comparing yield (pounds of fruit) to unit of tree size (square centimeters of trunk cross-section). Records were kept over an 8 year period. The yield efficiency of this new rootstock was rated 8% above that of trees on Domestic Bartlett seedling rootstocks.

7. Most trees on this new rootstock demonstrated an early-bearing tendency when compared to young trees on Bartlett seedling rootstocks. This tendency was more pronounced with trees of the Bartlett variety.

Most young Bartlett trees grafted to Old Home × Farmingdale #217 began producing some fruit in their third year in the orchard. This was compared to only light sporadic sets of fruit on Bartlett trees grafted to Domestic seedling rootstocks in their fourth growing season.

8. This new rootstock selection proved to be hardy in all areas where it was tested and is believed to be hardy wherever pears are grown.

9. The new rootstock is graft-compatible with all major commercially grown pear varieties.

10. Good root-anchorage was demonstrated in both the orchard and in the nursery.

11. Pear rootstock trees of the Old Home × Farmingdale #217 can be easily propagated by hardwood and softwood cuttings and/or by micropropagation methods (meristematic tissue culture). Such asexual reproductions have demonstrated that its distinctive characteristics and particularly including its "semi-standard" growth controlling character are stable and are transmitted without change through succeeding propagations and generations.

GENERAL AND DETAILED DESCRIPTION

Since Old Home × Farmingdale #217 is a variety intended to be used only as a rootstock for pear cultivars, the main detailed description and accompanying drawings will center on the vegetative parts rather than the flowers and fruits. This pear selection will be propagated only asexually rather than by seed, in order to maintain its clone characteristics. The accompanying pictures show typical specimens of this new clonal pear rootstock.

FIG. 1: This picture shows a one-year old shoot of Old Home × Farmingdale #217 taken from the cuttingbed showing its straight, upright and semi-branchless habit of growth.

FIG. 2: This picture shows typical leaves of Old Home × Farmingdale #217 showing their broad-ovate shape and the finely-serrated margins. The medium length petioles are shown here with long slender stipules at the base.

FIG. 3: This picture shows typical growth of Old Home × Farmingdale #217 in the nursery cuttingbed.

Figure 4:
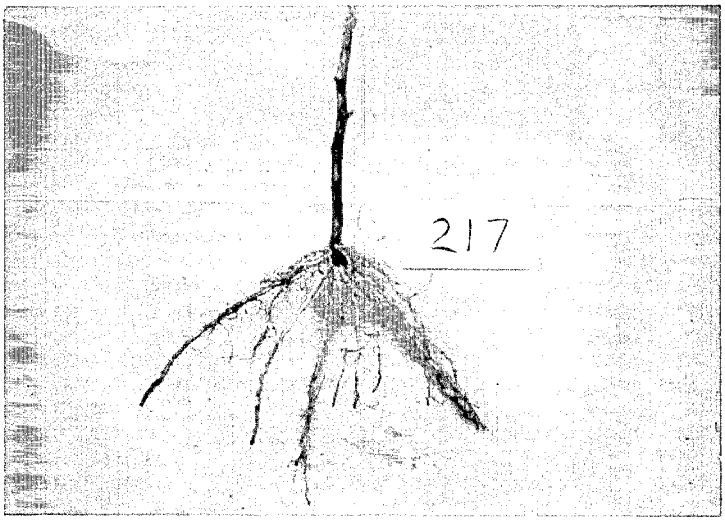

FIG. 4: This picture shows a rooted hardwood cutting of Old Home × Farmingdale #217 taken from the cutting bed showing typical root development at the basal cut.

DESCRIPTION OF VEGATATIVE CHARACTERISTICS

The following is a detailed description of the new pear rootstock's growth characteristics as observed on one year old shoots products from hardwood cuttings which were grown in a cuttingbed located in the propagation nursery at Forest Grove, Oreg. These observations were made during the late growing season after vigorous spring and summer growth had ceased but prior to fall leaf senescence. The new variety was also observed closely outdoors in the late fall during digging operations and again later in our tree storage warehouse where all stocks were evaluated for rooting characters prior to grading and storage. The characteristics described are those most often seen and used in the identification of a clonally propagated rootstock.

Colors of leaves and shoots herein described are based on their appearance at the site where stocks were grown, dug and stored. In those instances where a precise color assessment can be made, reference is to a Munsell Limit Color Cascade chart. In other instances, general color terms are used in accordance with their ordinary dictionary significance.

General habit:
- *Strength of growth.*—Vigorous, willowy, flexible.
- *Habit.*—Upright.
- *Branching.*—Few, thin, flexible.

Wood—summer:
- *Color.*—Green (22-11) on upper side, dark-green (21-13) on lower side.
- *Pubescence.*—None.
- *Texture.*—Smooth.

Wood—winter:
- *Stoutness.*—Willowy, flexible.
- *Diameter of shoots.*—$\frac{1}{4}$" between buds, 5/16" across buds, $\frac{3}{8}$" through buds.
- *Flexibility.*—Flexible.
- *Internodes.*—$1\frac{5}{8}$", medium.
- *Color.*—Olive-green (23-11) on upper side, brownish-green (24-11) on lower side.
- *Pubescence.*—None.
- *Texture.*—Smooth.

Lenticels:
- *Number.*—Few.
- *Conspicuousness.*—Summer conspicuous.
- *Shape.*—Mostly round, slightly raised.
- *Color.*—Whitish, turning to yellow-brown (27.9).
- *Distribution.*—Scattered.
- *Size.*—Small to medium, indistinct.

Leaves:
- *Size.*—Medium, length 3", breadth 1 9/16".
- *Shape.*—Broad-ovate, folded upward.
- *Base.*—Acute to cuneate, attenuated.
- *Apex.*—Acute, sometimes twisted.
- *Serrations.*—Finely-serrate, some teeth tipped with small glands.
- *Surface.*—Flat, few hairs along veins and midrib.
- *Margin.*—Folded upward.
- *Pose in relation to stem.*—Erect.
- *Color.*—Glossy-green (21-14) on upper surface, green (21-12) on lower surface.
- *Pubescence.*—Few hairs along veins and midrib on upper surface, none on lower surface.
- *Texture.*—Pliant, smooth, thin.
- *Color of tips of shoots.*—Yellowish-green (23-8) when still actively growing.

Petiole:
- *Pubescence.*—Slight on upper surface, smooth on lower surface.
- *Shape.*—Slender, slightly channeled.
- *Length.*—Medium, 15/16".
- *Color.*—Green (21-9), yellowish-green on new growth.
- *Pose.*—Erect.
- *Glands.*—Lacking.

Stipules (not always present):
- *Size.*—Very small.
- *Margin.*—Smooth.
- *Shape.*—Narrow, very slender.
- *Length.*—5/16".
- *Color.*—Light-green (21-12).
- *Pose.*—Slightly erect.

Buds:
- *Size.*—Small.
- *Shape.*—Short, conical, pointed.
- *Color.*—Brown, waxy.

*Pubescence.*—None.
*Pose.*—Appressed.

FLOWER AND FRUIT CHARACTERS

Flowers:
*Size.*—$1\frac{1}{4}''$ across, average 7 or 8 buds in a cluster.
*Color.*—White.
*Pedicels.*—$\frac{1}{2}''$ long, pubescent, greenish.

Fruit (no commercial value but useful for identification):
*Size.*—3" long, $2\frac{1}{4}''$ wide, large, uniform.
*Color.*—Yellow (26-5).
*Stem.*—$\frac{3}{4}''$ long, thick, curved.
*Shape.*—Oblong-ovate-pyriform, ribbed, with unequal sides.

GENERAL CHARACTERISTICS

Rootsuckering: Very rare.

Size control potential: "Semi-standard", about 85% of standard, less vigorous varieties slightly more reduced in size.

Yield efficiency: Highest of all rootstocks tested, average about 8% above trees on Domestic seedling stocks (*Pyrus communis*).

Compatibility: Graft-compatible with all major commercial fruiting varieties.

Rooting: Hardwood cuttings root well, roots arise mostly at basal cuts.

Root anchorage: Very good, well anchored in both orchard and nursery.

Hardiness: Hardy whenever pears are grown.

Disease resistance: Highly resistant to Fireblight (*Erwinia amylovora*), tolerant of the Pear Decline mycoplasma organism, index tested and shown to be free of known pear viruses.

Pest resistance: Average resistance to common pests of pear.

Early bearing ability: Early bearing demonstrated with Bartlett variety only, about 1 year ahead of Bartletts on Domestic seedling rootstocks.

I claim:

1. A new and distinct variety of pear tree referred to by the cultivar designation Old Home × Farmingdale #217 and substantially as herein shown and described characterized particularly by its ability to serve as a rootstock for grafting of pear tree cultivars to produce "semi-standard" pear trees; further characterized by its resistance to the Fireblight disease and its tolerance of the Pear Decline disease; further characterized by its non-rootsuckering habit, its hardiness, its excellent root-anchorage, its good compatibility with all major commercial pear varieties, its early bearing habit, and its ability to root easily and reproduce readily by hard and softwood cuttings.

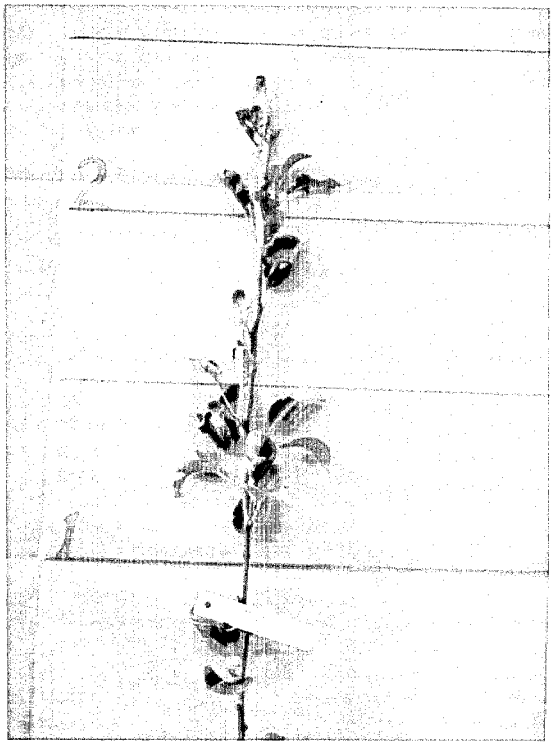
FIG. 1
FIG. 2
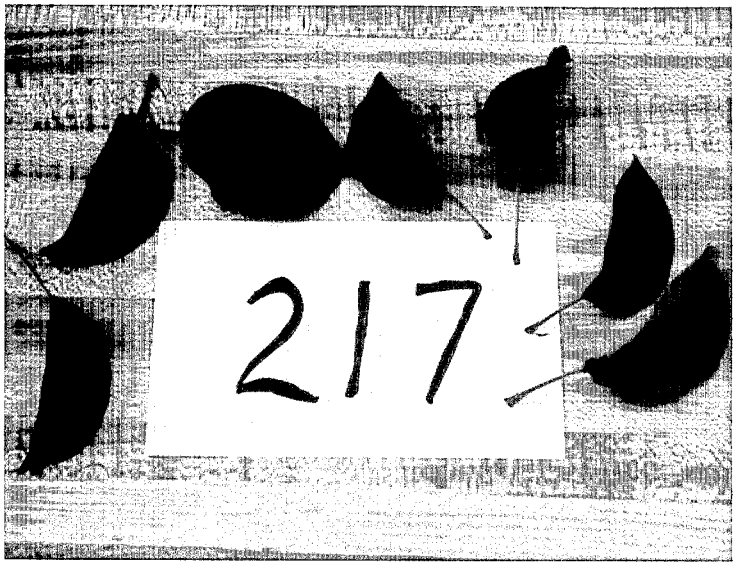

* * * * *